(12) United States Patent
Decker

(10) Patent No.: US 9,095,692 B2
(45) Date of Patent: Aug. 4, 2015

(54) METHOD FOR TREATING POISON IVY AND SIMILAR POISON PLANT INDUCED RASHES

(71) Applicant: Kate Delano-Condax Decker, Moorestown, NJ (US)

(72) Inventor: Kate Delano-Condax Decker, Moorestown, NJ (US)

(*) Notice: Subject to any disclaimer, the term of this patent is extended or adjusted under 35 U.S.C. 154(b) by 215 days.

(21) Appl. No.: 13/945,954

(22) Filed: Jul. 19, 2013

(65) Prior Publication Data
US 2014/0039421 A1    Feb. 6, 2014

Related U.S. Application Data

(60) Provisional application No. 61/679,255, filed on Aug. 3, 2012.

(51) Int. Cl.
*A61K 36/82* (2006.01)
*A61K 36/185* (2006.01)
*A61M 35/00* (2006.01)

(52) U.S. Cl.
CPC .................................. *A61M 35/003* (2013.01)

(58) Field of Classification Search
USPC .................................................. 424/729, 747
IPC .......................................... A61K 36/82,36/534
See application file for complete search history.

(56) References Cited

U.S. PATENT DOCUMENTS

| | | | |
|---|---|---|---|
| 5,888,515 A * | 3/1999 | Albert et al. | 424/738 |
| 6,579,543 B1 * | 6/2003 | McClung | 424/728 |
| 7,387,807 B2 * | 6/2008 | Callaghan et al. | 424/764 |
| 7,858,570 B2 * | 12/2010 | Hare | 510/139 |
| 8,067,358 B1 * | 11/2011 | Smith et al. | 514/1 |
| 8,449,879 B2 * | 5/2013 | Laurent-Applegate et al. | 424/93.7 |
| 2003/0077304 A1 * | 4/2003 | McCadden | 424/400 |
| 2004/0105905 A1 * | 6/2004 | Callaghan et al. | 424/764 |
| 2006/0058238 A1 * | 3/2006 | Laurent-Applegate et al. | 514/12 |
| 2007/0036843 A1 * | 2/2007 | Hirsh et al. | 424/443 |
| 2012/0045407 A1 * | 2/2012 | Kaur et al. | 424/62 |
| 2013/0243888 A1 * | 9/2013 | Ford | 424/690 |

FOREIGN PATENT DOCUMENTS

GB    2507563    *  5/2014

OTHER PUBLICATIONS

Scamahorn, C. Internet article entitled "Probaway—Itch". 2005. 3-pages. Obtained from http://www.probaway.com/Itch/itch.htm.*
Internet article entitled "Use a Hot Sppon to Instanly Relieve Itchy Bug Bites". Downloaded Feb. 9, 2015. 3-pages. Obtained from http://lifehacker.com/use-a-hot-spoon-to-instantly-relieve-itchy-bug-bites-615912899.*

* cited by examiner

*Primary Examiner* — Chris R Tate
(74) *Attorney, Agent, or Firm* — Stuart M. Goldstein

(57) ABSTRACT

A method for treating poison ivy and similar poison plant induced rashes utilizes a sealed pouch containing a mixture of anti-inflammatory, analgesic, and anti-oxidant property ingredients. The pouch is placed in a container filled with boiling water. The ingredients in the pouch permeate through the water. A metal applicator has a spoon-shaped section with a curved lower surface and a handle. The spoon-shaped section is inserted into the boiled herbal water mixture. The bottom surface of the curved lower surface of the spoon-shaped section is then momentarily placed on the pustule or red bump of the poison ivy. The applicator is then lifted up away from the area. Usually two or three touches with the applicator on the effected area will completely remove the itching and the itching and pustule will be entirely eliminated within twenty-four to forty-eight hours.

6 Claims, 3 Drawing Sheets

METHOD FOR TREATING POISON IVY AND SIMILAR POISON PLANT INDUCED RASHES

RELATED APPLICATION

The herein application claims the benefit of U.S. Appl. Ser. No. 61/679,255 filed on Aug. 3, 2012.

BACKGROUND OF THE INVENTION

Poison ivy, poison oak, poison sumac, and other varieties of poisonous plants are known to cause a variety of adverse effects to individuals who come into contact with these plants. Such effects range from the forming of pustules, red bumps or rashes on the skin to causing anaphylaxis or even death to those who are severely allergic to such plants. Contact with poison ivy and like plants can occur by brushing against the plants, from being near smoke when brush containing the plants are burned, and, as to these individuals with severe sensitivity, even walking near the plants. Individuals who spend many hours outdoors, e.g. gardeners, campers, joggers, outdoor sportsman, are especially vulnerable to poison ivy and like poisonous plants.

Common treatments for poison ivy usually contain the use of cortisone or other steroids, applied on the pustule rash to stop the itching for enough days until the ivy induced problem runs its course and heals. This usually takes from one week to ten days. However, cortisone can have serious side effects which can be harmful, sometimes causing damage to the kidneys and liver. Certain people experience other adverse or allergic reactions which preclude its use altogether.

In addition, many poison ivy medications and treatments are messy and gooey. These need to be covered by bandages to prevent staining of clothing and furniture. Other treatments just do not work effectively.

SUMMARY OF THE INVENTION

It is thus the object of the present invention to provide a method for eating poison ivy and similar poison plant induced rashes which overcomes the disadvantages and limitations of existing treatments.

The method of the present invention is effective virtually 100% of the time. In addition, it has the following other significant advantages:

The method of the present invention is safe.

The method of the present invention is completely organic and homeopathic.

The method of the present invention contains no cortisone, harmful chemicals or medicines, and no toxic ingredients.

The method of the present invention is effectively accomplished with no side effects.

The method of the present invention is clean and does not stain clothing or furniture.

The method of the present invention works in one or two applications in most cases. All evidence of itching and redness are generally completely gone within twenty-four to forty-eight hours.

The method of the present invention works effectively on poison ivy, poison sumac, poison oak, and similar poison plant-induced rashes.

These and other advantages and objectives are accomplished by the present invention, a method for treating poison ivy and similar poison plant-induced rashes which utilizes a sealed pouch containing a mixture of ingredients having anti-inflammatory, analgesic, and anti-oxidant properties. The method is accomplished by placing the sealed pouch in a heat-resistant container filled with boiling water. The ingredients in the pouch permeate through the water. A metal applicator, preferably made of stainless steel, has a spoon-shaped section with a curved lower surface and a handle extending from the spoon-shaped section. The spoon-shaped section is inserted into the boiling water. The bottom surface of the curved lower surface of the spoon-shaped section is then momentarily placed on the pustule or red bump of the poison ivy on the skin. The applicator is then lifted up away from the skin. Usually two or three touches on the poison ivy pustule or red bump with the applicator will completely remove the itching and the itching and redness or pustule will be entirely eliminated within twenty-four to forty-eight hours.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

DETAILED DESCRIPTION OF THE INVENTION

Figure 1:
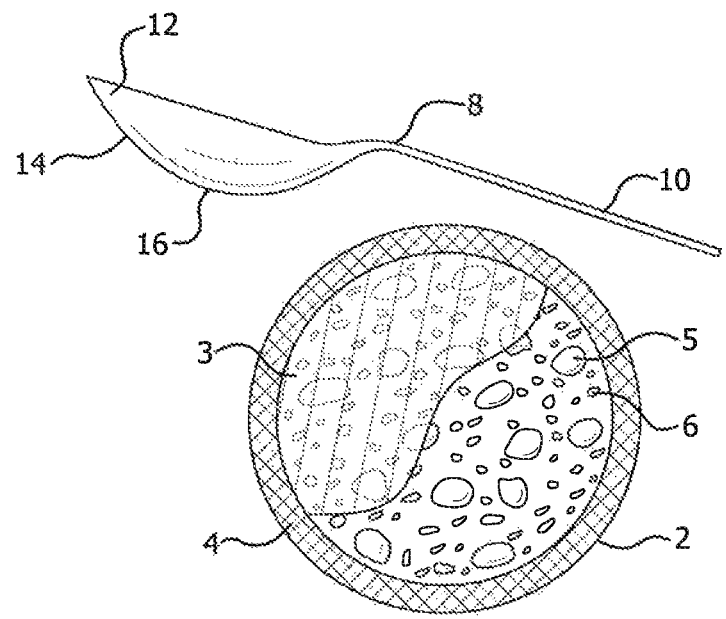
FIG. 1 shows a partially cut-away pouch and the applicator used in the method of the present invention.

FIG. 1 shows the key components utilized in the method of the present invention. Pouch 2 is made of lightweight permeable paper such as is found in tea bags. Pouch 2, having outer cover 3 sealed around its edges 4, contains an herbal mixture of anti-inflammatory, analgesic, and anti-oxidant ingredients, for instance green tea 5 and camphor 6. These ingredients have healing and soothing properties for the skin and are sealed within the pouch.

Although green tea and camphor are cited herein, the following substances, which also have anti-inflammatory, analgesic, and anti-oxidant characteristics, can be used in selected combinations as well to heal and sooth the skin:

| | |
|---|---|
| Green tea | *Aloe Vera* |
| Camphor | Evening primrose oil |
| Menthol | Ginger |
| MSM (sulfur source for skin & body tissues) | Gotu kola |
| Emo oil | *Ginkgo* |
| Menthol | Juniper |
| Glucosamine | Lavender oil |
| Chondroitin | Licorice |
| Capsaicnoid | Marjoram |
| Arnica extract | Meadow sweet |
| Coriander oil | Passion flower |
| Chamomile (Roman) | Quercetin |

| | |
|---|---|
| Chamomile oil | Salicinum |
| Willow bark extract | Wild yam |
| Feverfew extract | Wintergreen |
| St. John's wort | Wood betony |
| Kava Kava extract | Wormwood |
| Nettle leaf | Marigold |
| Acetylsalicylic acid | *Boswellia* |
| Bala | Borage |
| Black cohosh | Bromelain |
| Bugbane | Buvduck |
| Squawroot | *Calendula* |
| *Calendula* | Dandelion |
| Cayenne | Omega 3 fatty acid |
| Devils' claw rout | Omega 6 fatty acid |
| Witch hazel | Linoleic acid |
| Elderflower | *Ginseng* |
| Hawthorne | Kaempferol |
| Life root | Golden ragwort |
| Linden | Neem |
| Padma 28 | Quercetin |
| Turmeric | Yucca |
| Grape seed | |

Applicator 8, preferably made of stainless steel or similar metal with heat retention properties, comprises handle 10 and closed in, solid spoon-shaped section 12 with curved lower surface 14 having bottom surface 16.

Figure 2:
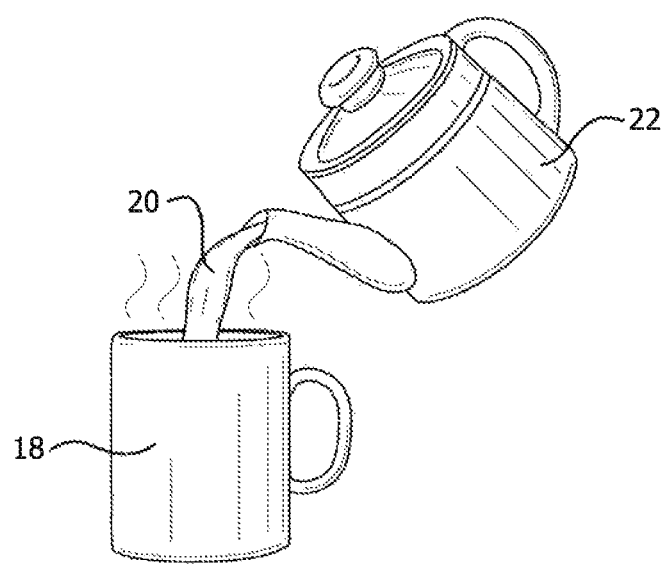
FIG. 2 depicts the first step of the method of the present invention.
Figure 3:
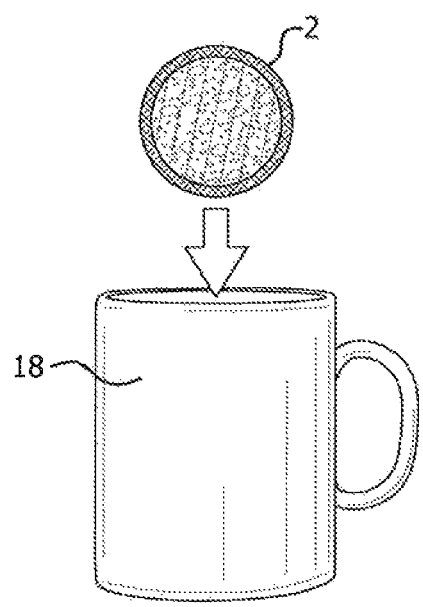
FIG. 3 depicts the next step of the method of the present invention, inserting the pouch into boiling water within a heat resistant container.

The method of the present invention should be performed as soon as possible after an individual contacts poison ivy, poison oak, poison sumac, or similar poison plant. FIG. 2 depicts the step of pouring boiling water 20 from kettle 22 or like vessel into a heat resistant container, such as mug 18. It is contemplated that container 18 will be made of ceramic which will maintain the water at the desired temperature. The container should not be glass or metal. Pouch 2 is then placed within heat-resistant container 18, shown in FIG. 3, where the boiling water soaks into pouch 2 and causes its soothing ingredients to be disbursed and permeated through the now herbal soaked water 21.

Figure 4:
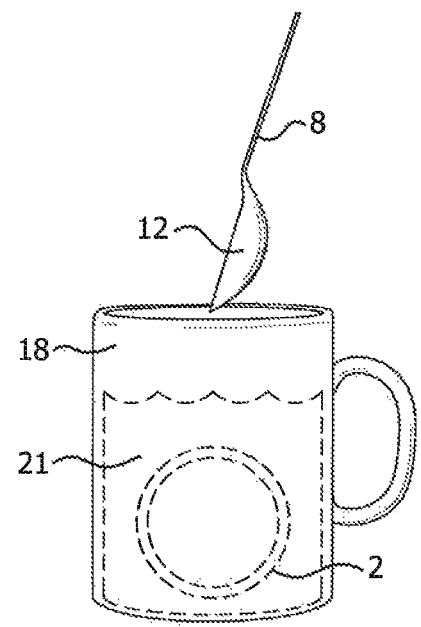
FIG. 4 depicts the subsequent step of the method of the present invention, inserting the applicator into herbal soaked boiling water within a heat resistant container.
Figure 5:
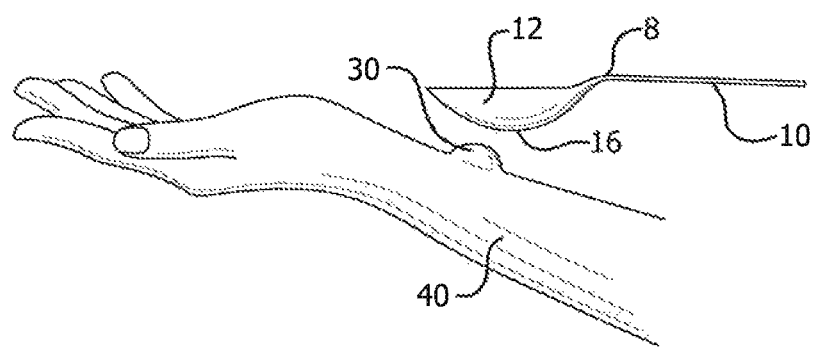
FIG. 5 depicts the final step of the method of the present invention in which the applicator, having been removed from the container, is placed on a red bump or pustule caused by poison ivy on the skin of the user.

As depicted in FIG. 4, spoon-shaped section 12 of applicator 8 is placed into boiling herbal water 21 where it is withdrawn after approximately five seconds. Applicator 8 is shaken once or twice to remove excess water. Bottom surface 16 of spoon-shaped section 12 is then placed on poison ivy pustule or red bump 30, as shown in FIG. 5, without touching the surrounding skin of arm 40 of the affected individual. The touch from applicator 8 should be momentary, for example, lasting approximately one-half second. Applicator 8 should not be pressed down on the effected area, but instead it should barely touch the effected area and be immediately lifted up and away from the skin. The skin surrounding the pustule or effected area should not be touched.

The process of dipping applicator 8 into herbally treated hot water 21 should be repeated. Usually two or three successive touches on the pustule or affected area with applicator will 8 remove the itching. If the itching continues longer than one minute, the contents of container 18 should be discarded and new boiling water and with a new herbal pouch 2 should be used and the process repeated.

It has been found that if itching continues after the procedure, anywhere from a few minutes to several hours, the process should be repeated. In most cases, the pustule, itching, and redness in the area will be completely gone within twenty-four to forty-eight hours, except in cases where treatment was not begun promptly and scabs and extreme inflammation are allowed to develop. In such cases, healing may take longer to be resolved.

A critical component to the success of the method of the present invention resides in the use of specifically designed applicator 8. When heated, bottom surface 16 of spoon-shaped section 12 of the applicator positioned directly and solely on the affected area and not on adjacent, healthy skin. This serves to dry up and heal only the pustule and redness on the skin. Adjacent areas of the skin area are not damaged or marked.

While it is generally known that utilizing heat on poison ivy rashes and pustules constitutes a source of treatment, such crude applications of heat on the skin, for instance by blowing hot air from a hair dryer, is random and imprecise. It is impossible to maintain the proper temperature of the heated air being applied and delivering heat in this shotgun manner causes harm to unaffected areas. The present method address and solves these significant problems by use of applicator 8 and the exacting application of heat at the precise temperature directly and solely to the pustule or other effected location. In this manner, only the affected area is treated, and it is treated effectively without damage to adjacent healthy skin.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. A method of treating pustules and other affected areas on the skin caused by poison ivy, poison oak and/or poison sumac comprising the steps of:
   providing a sealed pouch containing an herbal mixture of green tea and camphor;
   providing a heat-resistant container;
   pouring boiling water into the container;
   placing the pouch within the container;
   allowing the pouch to soak in the boiling water, thus creating an aqueous extract of the herbal mixture within the container, wherein the aqueous extract has anti-inflammation, analgesic, and anti-oxidant properties;
   providing an applicator with a spoon-shaped section having a curved lower surface with a bottom surface and a handle extending from the spoon-shaped section;
   inserting the spoon-shaped section into the aqueous extract in the container;
   withdrawing the spoon-shaped section from the aqueous extract;
   touching only the pustule and not the skin with the bottom surface of the spoon-shaped section of the applicator;
   lifting the applicator off and away from the pustule after touching it with the spoon-shaped section; and
   repeating the steps of inserting the spoon-shaped section into the aqueous extract, withdrawing the spoon-shaped section from the water, and touching only the pustule and not the skin with the bottom end of the spoon-shaped section of the applicator.

2. The method as in claim 1 comprising the further steps of maintaining the spoon-shaped section of the applicator in the aqueous extract for approximately five seconds after inserting it into the aqueous extract and before withdrawing the spoon-shaped section.

3. The method as in claim 1 comprising the further step of shaking the applicator to remove excess liquid after withdrawing it from the aqueous extract in the container.

4. The method as in claim 1 comprising the further step of maintaining the bottom surface of the spoon-shaped section of the applicator on the pustule for approximately one-half second before lifting the applicator off and away from the pustule.

5. The method as in claim 1 wherein the container is made of ceramic material.

6. The method as in claim 1 wherein the applicator is made of stainless steel.

* * * * *